United States Patent [19]  [11] 4,004,033
Schellenbaum  [45] Jan. 18, 1977

[54] CERTAIN ALKYLPHENOLS USED TO CONTROL BACTERIA

[75] Inventor: Max Schellenbaum, Muttenz, Switzerland

[73] Assignee: Ciba-Geigy Corporation, Ardsley, N.Y.

[22] Filed: Mar. 24, 1975

[21] Appl. No.: 561,521

Related U.S. Application Data

[63] Continuation-in-part of Ser. No. 496,799, Aug. 12, 1974, abandoned.

[30] Foreign Application Priority Data

Aug. 16, 1973 Switzerland .................... 11806/73

[52] U.S. Cl. .............................................. 424/347
[51] Int. Cl.² ........................................ A01N 9/26
[58] Field of Search .................................. 424/347

[56] References Cited

UNITED STATES PATENTS 2,900,301 8/1959 Schmidt .................... 424/347 X
R20,683 3/1938 Blicke .................... 424/347 X

OTHER PUBLICATIONS

Chemical Abstracts 5a:9956 g, (1963).

*Primary Examiner*—Leonard Schenkman
*Attorney, Agent, or Firm*—Frederick H. Rabin

[57] ABSTRACT

The use of compounds of formula I

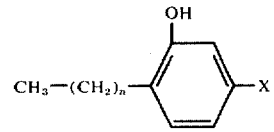

wherein

X represents chlorine or bromine and $n$ denotes an integer from 1 to 6 for combating harmful microorganisms is disclosed.

4 Claims, No Drawings

CERTAIN ALKYLPHENOLS USED TO CONTROL BACTERIA

CROSS-REFERENCE TO RELATED APPLICATION

This application is a continuation-in-part of application Ser. No. 496,799 filed Aug. 12, 1974, now abandoned.

The present invention relates to a method for the control of harmful microorganisms by applying to said microorganisms a microbicidally effective amount of a compound of formula I

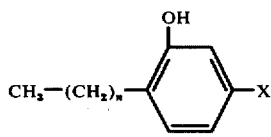

wherein
X represents chlorine or bromine, and
n denotes an integer from 1 to 6.

The use of a number of alkylphenols for the control of microorganisms, especially of gram-positive bacteria, is already known (see K. H. Wallhauser and H. Schmidt, "Sterilisation, Desinfection, Konservierung, Chemotherapie" (Sterilisation, Disinfection, Preservation, Chemotherapy), Georg Thieme Verlag, 1967).

It has now been found that, surprisingly, the alkylphenols used according to the invention, which as compounds are in some cases known (see K. A. Thakar, Journal of the Indian Chemical Society 40, 539, 1963), are, by virtue of their special substitution, highly effective also against gramnegative bacteria and against fungi. The compounds advantageously have an exceptionally wide range of action but only slight toxicity. A particular advantage of the compounds used according to the invention is that, even with relatively small concentrations, they have an action ranging from a simple inhibitory effect up to a complete destruction of the microorganisms to be controlled. With regard to the technical aspects of application, the colourlessness of the compounds of formula I is of special value.

The compounds of formula I can be prepared by the reduction of ketones of formula II

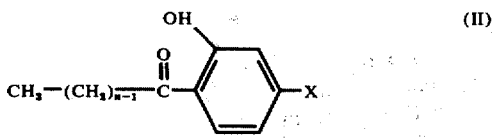

wherein X and n have the above given meanings.

Reduction of the ketones can be performed, for example, by the method of Huang-Minlon (see Huang-Minlon, Journal of the American Chemical Society 68, 2487, 1946), wherein the corresponding hydrazone is decomposed in an inert solvent at elevated temperature, with the aid of an inorganic base, to the hydrocarbon. The Clemmensen reduction too (see E. Clemmensen, Berichte der deutschen Chemischen Gesellschaft 46, 1837, 1913) constitutes a good method for the preparation of the alkylphenols from the corresponding ketones. The reduction in this case is performed by heating of the ketones with amalgamated zinc and hydrochloric acid in the presence of an organic solvent.

The ketones of formula II employed as starting materials are known (see K. A. Thakar, Journal of the Indian Chemical Society 40, 539, 1963), or are prepared by methods known per se, e.g. from the corresponding alkanecarboxylic acid phenyl esters by the Fries reaction (see Baltzly et al. Journal of the American Chemical Society 77, 2522, 1955, or G. A. Olah, Friedel-Crafts and Related Reactions 1964, p. 499).

The compounds of formula I have good solubility in organic solvents. Their water-soluble salts, especially the alkali metal salts and alkaline-earth metal salts, are likewise effective and are of particular importance in the case of application in an aqueous medium and in soaps.

The use of the antimicrobial compounds of formula I is possible on a very wide basis, particularly for disinfection purposes, for example for the disinfection of equipment used in the industrial preparation of food and beverages, for the disinfection of floors, stables, swimming-pools and for disinfection purposes in hospitals. Further, the compounds of formula I can be used for the disinfection of surfaces, for example surfaces of shaped articles made of plastic material, and furniture.

The following are mentioned as examples of commercial products that can be preserved with the aid of compounds of formula I:

Glues, bonding agents, coating agents, textile auxiliaries and finishing agents, dyeing and printing pastes and similar preparations based on organic and inorganic dyestuffs or pigments, and also products which contain as additives casein or other organic compounds. Also wall and ceiling coatings, e.g. those which have a colour binder containing albumin, are protected against infestation by pests by an addition of the compounds. An application of the said compounds for the protection of wood is likewise possible. The compounds of the invention can also be used as preservatives in the cellulose and paper industry for, inter alia, the prevention of the known formation of mucilage, caused by microorganisms, in the equipment used for paper making.

The action of the compounds of formula I may be utilised also for imparting to plastics a preserving and disinfecting finish. It is advantageous with the use of plasticisers that the antimicrobial agent be dissolved or dispersed in the plasticiser before being added to the plastics, and it is preferable that the distribution of the antimicrobial agent in the plastics be as uniform as possible. The plastics having antimicrobial properties can be used for consumer products of all kinds where it is desired that the products concerned be effectively protected against the widest variety of germs, such as bacteria and fungi; they may be used, for example, for foot mats, bath-room curtains, articles for seating, foot gratings in swimming baths, wall coverings, etc. By incorporation of the said compounds into the appropriate wax compositions and polishing preparations, there are obtained floor and furniture preserving agents having a disinfecting finish.

The compounds of formula I are advantageously used for imparting a preserving and disinfecting finish to fibres and textiles; they can be applied to natural and synthetic fibres and remain permanently effective there against harmful (also pathogenic) microorganisms, e.g. fungi and bacteria. The compounds can be added before, simultaneously with, or after a treatment of these textiles with other substances, e.g. dyeing or printing pastes, flameproofing agents, soft-handle-imparting agents and other finishing agents.

Textiles thus treated provide protection against the occurrence of perspiration odour, which is caused by microorganisms.

The forms in which the active substances of formula I are applied can correspond to the usual formulations. The agents used for the finishing or protecting of textiles should contain the active substances in a finely dispersed form. The preparations employed are therefore, in particular, solutions, dispersions and emulsions of the active substances. Aqueous dispersions can be obtained, for example, from pastes or concentrates, and can be used in the liquid form or as aerosol.

The aqueous solutions or dispersions thus advantageously contain surfactants, for example, anion-active compounds, such as soaps and other carboxylates (e.g. alkali salts of higher fatty acids), derivatives of acids containing sulphur and oxygen (e.g. sodium salt of dodecylbenzenesulphonic acid, water-soluble salts of sulphuric acidmonoesters of higher-molecular alcohols or of their polyglycol ethers, such as, for instance, soluble salts of dodecyl alcohol sulphate or of dodecyl alcohol polyglycol ether sulphate), derivatives of acids containing phosphorus and oxygen (e.g. phosphates), derivatives with acid (electrophilic) nitrogen in the hydrophilic group (e.g. disulphinic salts), cation-active surfactants, such as amines and salts thereof (e.g. lauryldiethylenetriamine), onium compounds, amine oxides or nonionic surfactants, such as polyhydroxy compounds, surfactants based on mono- or polysaccharide, higher-molecular acetylene glycols, polyglycol ethers (e.g. polyglycol ethers of higher fatty alcohols, polyglycol ethers of higher-molecular-alkylated phenols). The liquor can in addition contain the usual auxiliaries, such as water-soluble perborates, polyphosphates, carbonates, silicates, optical brighteners, softeners, acid reacting salts, such as ammonium or zinc-silicofluoride, or certain organic acids, such as oxalic acid, also finishing agents, e.g. those based on synthetic resin or on starch.

The textile materials can be impregnated with the active substances by means of, for example, hot or cold aqueous dyeing, bleaching, chroming or aftertreatment baths, with various textile-finishing processes, such as the padding or exhaust process, being suitable.

On account of better solubility in organic solvents, the active substances of the invention are also very suitable for application from non-aqueous media. The materials to be finished or protected can be simply impregnated with the solutions. Suitable organic solvents are, for example, trichloroethylene, methylene chloride, hydrocarbons, propylene glycol, methoxyethanol, ethoxyethanol or dimethylformamide, to which may also be added dispersing agents (e.g. emulsifiers, such as sulphated castor oil, fatty alcohol sulphates, etc.) and/or other auxiliaries.

Depending on the purpose of application, the content of active substances can according to the present invention be between 0.1 and 50 g, preferably between 1 and 30 g, of active substance per liter of treatment liquid.

The active substances of formula I can be used on their own or together with other known antimicrobial textile-protective agents.

Suitable as textiles to be treated or protected are both fibres of natural origin, such as those containing cellulose, e.g. cotton, or containing polypeptide, e.g. wool or silk, and fibre materials of synthetic origin, such as those based on polyamide, polyacrylonitrile or polyester, or mixtures of these fibres.

In most cases, the textile materials are adequately protected against infestation by fungi and bacteria by a content of active substance of 0.01 to 5%, preferably 0.1 to 3%, relative to the weight of the textile materials.

By a combination of the active substances of the invention with interface-active, particularly 'wash-active', substances, detergents and cleansing agents having excellent antibacterial or antimycotic action are obtained. They are likewise suitable as antimicrobial cleansing agents in the foodstuff and drink industry, e.g. for breweries, dairies, cheese-making establishments and slaughterhouses.

The applicability of compounds of formula I for the control of microorganisms, particularly of bacteria and fungi, and for the preserving of organic materials and objects against infestation by microorganisms is very extensive. Thus, for example, they can be incorporated direct into the material to be preserved, e.g. into material having a synthetic resin base, such as polyamides and polyvinyl chloride, into paper-treatment liquors, into printing thickeners made from starch or cellulose derivatives, into lacquers and paints which contain, for example, casein, into cellulose, viscous spinning solutions, paper, into animal mucus or oils, into permanent coatings based on polyvinyl alcohol, cosmetic articles, and into ointments or powders. They can also be added to preparations of inorganic or organic pigments for the painting industry, to softeners, etc..

The compounds of formula I can be used moreover in the form of their organic solutions, e.g. as so-called sprays, or as dry-cleaning agents, or for the impregnation of wood, suitable organic solvents being preferably solvents immiscible with water, particularly petroleum fractions, but also solvents miscible with water, such as lower alcohols, e.g. methanol or ethanol or ethylene glycol monomethyl ether, or -monoethyl ether. A number of the new compounds can be used also in aqueous solution.

Furthermore, they can be used together with wetting or dispersing agents, in the form of their aqueous dispersions, e.g. for the preservation of substances which tend to rot, such as for the preservation of leather, paper, etc..

Solutions or dispersions of active substances, which can be employed for the preservation of these materials, preferably have an active-substance content of at least 0.005 g/liter, e.g. 0.01 to 5, preferably 0.1 to 3 g/liter.

EXAMPLE 1

128.6 g of 3-chlorophenol is dissolved in 400 ml of benzene and 79.1 g of anhydrous pyridine. An addition is then made dropwise at 5°–10° C within 25 minutes, with stirring, of 92.5 g of propionic acid chloride. The temperature of the reaction mixture is allowed to rise to 25° C; the precipitated pyridine hydrochloride is filtered off and the benzene solution is washed with water and, after drying by means of sodium sulphate, completely concentrated in a water-jet vacuum. The resulting propionic acid-3-chlorophenyl ester (175.4 g) is heated to 75°–80° C, and 267 g of anhydrous aluminium chloride is added in the course of 30 minutes. The reaction melt is heated for a further 5 hours at 100° C, and thereupon poured, with stirring, into 4 liters of ice water. The crystalline product is filtered off, washed with water and dried in vacuo. There is thus obtained 160.1 g of 2-hydroxy-4-chloropropiophenone, M.P. 50°–52° C.

A mixture of 158.0 g of 2-hydroxy-4-chloropropiophenone, 255 g of hydrazine hydrate, 286 g of potassium hydroxide and 700 ml of diethylene glycol is refluxed for 3 hours. The excess hydrazine hydrate is distilled off, and the reaction solution is subsequently heated for 2½ hours at 195°–205° C. It is then stirred into 4 liters of ice water, acidified with concentrated hydrochloric acid and extracted with chloroform. The chloroform solution is dried by means of sodium sulphate and then concentrated by evaporation. There is isolated from the resulting oil by high-vacuum distillation the compound of the formula

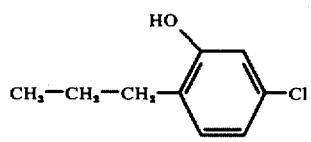

The yield is 122.5 g; B.P. 61°–65°/0.04 mm Hg.

The procedure of Example 1 or a method described in the foregoing can be used to prepare the compounds according to formula I which are listed in the following Table A.

Table A

| Compound No. | X | n | Physical data |
| --- | --- | --- | --- |
| 1 | Cl | 2 | oil (boiling point 61–65° C/0.04 mm Hg) |
| 2 | Cl | 1 | 52–53° C |
| 3 | Cl | 3 | oil (boiling point 130° C/0.05 mm Hg) |
| 4 | Br | 1 | 48–50° C |
| 5 | Br | 2 | oil (boiling point 72–75° C/0.04 mm Hg) |
| 6 | Cl | 4 | oil (boiling point 90–91° C/0.1 mm Hg) |
| 7 | Br | 3 | oil (boiling point 83° C/0.1 mm Hg) |
| 8 | Cl | 5 | oil (boiling point 91° C/0.1 mm Hg) |
| 9 | Br | 4 | oil (boiling point 86–89° C/0.08 mm Hg) |
| 10 | Cl | 6 | oil (boiling point 91–92° C/0.1 mm Hg) |

Determination of the minimum inhibiting concentrations (MIC) against bacteria and fungi Stock solutions (1.5%) of the compounds of formula I in methylcellosolve are prepared, and these are subsequently diluted so that the incorporation of 0.3 ml of the stock solution in each case and of each dilution into 15 ml each time of warm nutrient-agar produces a concentration series of 300, 100, 30, 10, 3, 1, and so forth, ppm of active substance in the agar. The mixtures whilst still warm are poured into dishes and, after solidification, inoculated with the test organisms.

After an incubation of 48 hours at 37° C (bacteria) and 5 days at 28° C (fungi), the minimum concentration (ppm) of the active substances with which the growth of the test organisms is inhibited is determined.

The values for the minimum inhibiting concentration (MIC) in the case of compounds No. 1 to 10 against Gram-positive and Gram-negative bacteria and fungi are given in the following table:

| Microorganism | Minimum inhibiting concentration for compound No. | | | | | | | | | |
| --- | --- | --- | --- | --- | --- | --- | --- | --- | --- | --- |
| | 1 | 2 | 3 | 4 | 5 | 6 | 7 | 8 | 9 | 10 |
| Staphylococcus aureus SG 511 | 18 | 16 | 7 | 80 | 15 | 3 | 7 | 2 | 3 | 2 |
| Streptococcus faecalis ATCC 10541 | 30 | 150 | 23 | 130 | 30 | 9 | 18 | 3 | 7 | 3 |
| Bacillus subtilis ATCC 6633 | 30 | 90 | 13 | 100 | 23 | 3 | 9 | 2 | 3 | 2 |
| Escherichia coli NCTC F196 | 14 | 30 | 6 | 30 | 16 | 3 | 3 | 3 | 3 | 3 |
| Salmonella pullorum VBIZ | 10 | 70 | 12 | 30 | 15 | 7 | 13 | 8 | 15 | 10 |
| Salmonella cholerae-suis VBIZ | 30 | 130 | 30 | 90 | 30 | 14 | 13 | 18 | 18 | >300 |
| Bordetella bronchiseptica TSA 742 | 30 | 30 | 17 | 30 | 30 | 15 | 12 | 27 | 18 | >300 |
| Proteus vulgaris ATCC 9484 | 19 | 90 | 13 | 30 | 22 | 6 | 11 | 3 | 7 | 10 |
| Trichophyton mentagrophytes ATCC 9533 | 11 | 17 | 6 | 18 | 12 | 3 | 3 | 3 | 3 | 3 |
| Candida albicans ATCC 10259 | 30 | 30 | 18 | 30 | 30 | 11 | 14 | 11 | 10 | 10 |
| Candida albicans M 500 | 30 | 30 | 19 | 30 | 30 | 12 | 18 | 11 | 13 | 30 |
| Aspergillus elegans M 3637 | 30 | 30 | 30 | 30 | 30 | 17 | 23 | 19 | 18 | 120 |

Determination of the microbicidal action

A. In order to determine whether the active substances had destroyed the test germs (biocidal effect) or had merely inhibited them in their growth (biostatic effect), sterile filter paper disks of 20 mm diameter are placed on the inoculation sites of the germs exhibiting no growth, and, after a contact time of 30 minutes, the germs transferred by means of these disks to sterile agar blocked with respect to the active substances with Tween 80. The contact time is again 30 minutes. If no growth of the transferred germs on the secondary agar-dish is observed, the germs will have been destroyed by the active substance in the first dish, i.e. the active substance in the concentrations concerned has a biocidal action on the germs examined.

The following additional test is carried out for confirmation of the preceding finding:

B. Active substances of formula I are used to prepare the following solutions:
5%: of active substance,
5%: of Na-N-cocos-β-aminopropionate,
20%: of permutite water,
70%: of ethylcellosolve (ethylene glycol monoethyl ether).

Aliquot parts of these solutions are converted with sterile distilled water into emulsions of 1000 ppm, 500 ppm, 250 ppm and 125 ppm active-substance content.

Samples of 9.9 ml of the emulsions are inoculated with 0.1 ml of germ suspensions (ca. $10^7$ germs/ml).
Test organisms:
*Staphylococcus aureus,*
*Streptococcus faecalis*
*Bacillus subtilis,*
*Proteus vulgaris.*

After an action time of one minute, a loop of the inoculated emulsions is placed in each case into 10 ml of sterile brain-heart-infusion-broth; after an incubation time of 24 hours at 37°, the brain-heart-infusion-broth is examined for cloudiness (germ growth).

The examined compounds of formula I exhibited in the above tests a biocidal action.

APPLICATION ON TEXTILE MATERIAL

Agar Diffusion Test

A sample of a reinforced cotton web (121 g per square meter) is impregnated with a solution of a test compound of formula I in ethyl cellosolve and subsequently squeezed out between two aluminum foils in a manner such that 2500 ppm of the active substance remain thereon.

After drying in the air the sample is tested in the Agar Diffusion Test (modified AATCC test method 90, 1970) against the following microorganisms:

Bacteria:
  Staphylococcus aureus ATCC 6538
  Escherichia coli NCTC 8196
  Proteus mirabilis NCTC 8309

Fungi:
  Candida albicans ATCC 10259
  Trichophyton mentagrophytes ATCC 9533

The test plates consist of a two-layer agar, i.e. of a basic layer which is not inoculated and of a top layer which is inoculated.

Nutrient agar is used for bacteria while mycophil agar is used for fungi.

In order to obtain the Trichophyton agar a filtrated germ suspension is poured on the congealed basic layer and, after solidification of the inoculated top layer, discs of the cotton web treated with the active substance having a diameter of 20 mm are placed thereon. The agar plates inoculated with bacteria and with Candida albicans are incubated for 24 hours at 37° C whereas the plates inoculated with Trichlphyton mentagrophytes are incubated for 3 to 4 days at 28° C. At the end of the incubation-period the test plates are evaluated by measuring the inhibition zone. If no inhibition zone has been developed the growth of microorganisms under the cotton discs is checked by means of a magnifying glass.

The results of the Agar Diffusion Test are given in the following table:

| | Micro-organism | Staphylococcus aureus ATCC 6538 | | Escherichia coli NCTC 8196 | | Proteus mirabilis NCTC 8309 | | Candida albicans ATCC 10259 | | Trichophyton mentagrophytes ATCC 9533 | |
|---|---|---|---|---|---|---|---|---|---|---|---|
| Compound No. | | inhibition zone (mm) | growth under disc | inhibition zone (mm) | growth under disc | inhibition zone (mm) | growth under disc | inhibition zone (mm) | growth under disc | inhibition zone (mm) | growth under disc |
| 3 | | 2 | — | 2 | — | 2 | — | 2 | — | 35 | — |
| 5 | | 0 | — | 3 | — | 0 | — | 0 | ± | 0 | — |
| 6 | | 5 | — | 10 | — | 3 | — | 5 | — | 35 | — |
| 7 | | 6 | — | 18 | — | 2 | — | 5 | — | 35 | — |

— no growth
± partial growth

What is claimed is:

1. A method for inhibiting the growth of bacteria which comprises applying thereto a growth-inhibiting amount of a compound of the formula

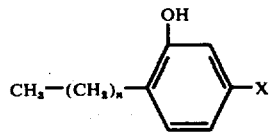

wherein
  X represents chlorine or bromine and
  n denotes an integer from 1 to 6.

2. A method according to claim 1 in which the compound is 2-ethyl-5-chlorophenol.

3. A method according to claim 1 in which the compound is 2-n-propyl-5-chlorophenol.

4. A method according to claim 1 in which the compound is 2-n-butyl-5-chlorophenol.